(12) United States Patent
Laks

(10) Patent No.: US 6,902,558 B2
(45) Date of Patent: Jun. 7, 2005

(54) ASPIRATOR TIP

(75) Inventor: Lawrence Laks, Bellevue, WA (US)

(73) Assignee: MicroSurgical Technology, Inc., Redmond, WA (US)

( * ) Notice: Subject to any disclaimer, the term of this patent is extended or adjusted under 35 U.S.C. 154(b) by 41 days.

(21) Appl. No.: 10/388,207

(22) Filed: Mar. 11, 2003

(65) Prior Publication Data

US 2003/0199883 A1 Oct. 23, 2003

Related U.S. Application Data

(60) Provisional application No. 60/363,465, filed on Mar. 11, 2002.

(51) Int. Cl.$^7$ .............................................. A61M 31/00
(52) U.S. Cl. ......................................... 604/521; 604/35
(58) Field of Search .............................. 604/27, 28, 30, 604/35, 39, 48, 521; 607/107

(56) References Cited

U.S. PATENT DOCUMENTS

| | | | | |
|---|---|---|---|---|
| 3,753,439 A | * | 8/1973 | Brugarolas et al. | 604/43 |
| 3,805,787 A | | 4/1974 | Banko | |
| 3,823,720 A | * | 7/1974 | Tribble | 604/43 |
| 3,996,935 A | | 12/1976 | Banko | |
| 4,487,600 A | | 12/1984 | Brownlie et al. | |
| 4,493,694 A | | 1/1985 | Wuchinich | |
| 4,652,255 A | * | 3/1987 | Martinez | 604/27 |
| 4,710,180 A | | 12/1987 | Johnson | |
| 5,151,083 A | | 9/1992 | Pichler | |
| 5,188,589 A | * | 2/1993 | Wypych et al. | 604/22 |
| 5,217,465 A | | 6/1993 | Steppe | |
| 5,242,449 A | | 9/1993 | Zaleski | |
| 5,282,786 A | * | 2/1994 | Ureche | 604/22 |
| 5,364,405 A | | 11/1994 | Zaleski | |
| 5,514,086 A | | 5/1996 | Parisi et al. | |
| 5,547,473 A | * | 8/1996 | Peyman | 604/27 |
| 5,558,634 A | * | 9/1996 | Mitchell | 604/35 |
| 5,718,677 A | | 2/1998 | Capetan et al. | |
| 6,258,070 B1 | * | 7/2001 | Kaldany | 604/264 |
| 6,361,520 B1 | * | 3/2002 | Rockley | 604/22 |
| 6,402,677 B1 | * | 6/2002 | Jacobs | 600/7 |
| 6,428,501 B1 | * | 8/2002 | Reynard | 604/27 |
| 2004/0133156 A1 | * | 7/2004 | Diaz et al. | 604/96.01 |

* cited by examiner

Primary Examiner—Sharon Kennedy
(74) Attorney, Agent, or Firm—Christensen O'Connor Johnson Kindness PLLC

(57) ABSTRACT

An elongated, rigid cannula has a peripheral wall defining a central bore and a side port for introduction of material into the bore. A covering of resilient, flexible material is provided in the area of the side port, with a corresponding aperture aligned with the port of the cannula. The aperture of the resilient covering can be somewhat smaller than the underlying cannula port, forming a resilient margin that overhangs and surrounds the port.

15 Claims, 4 Drawing Sheets

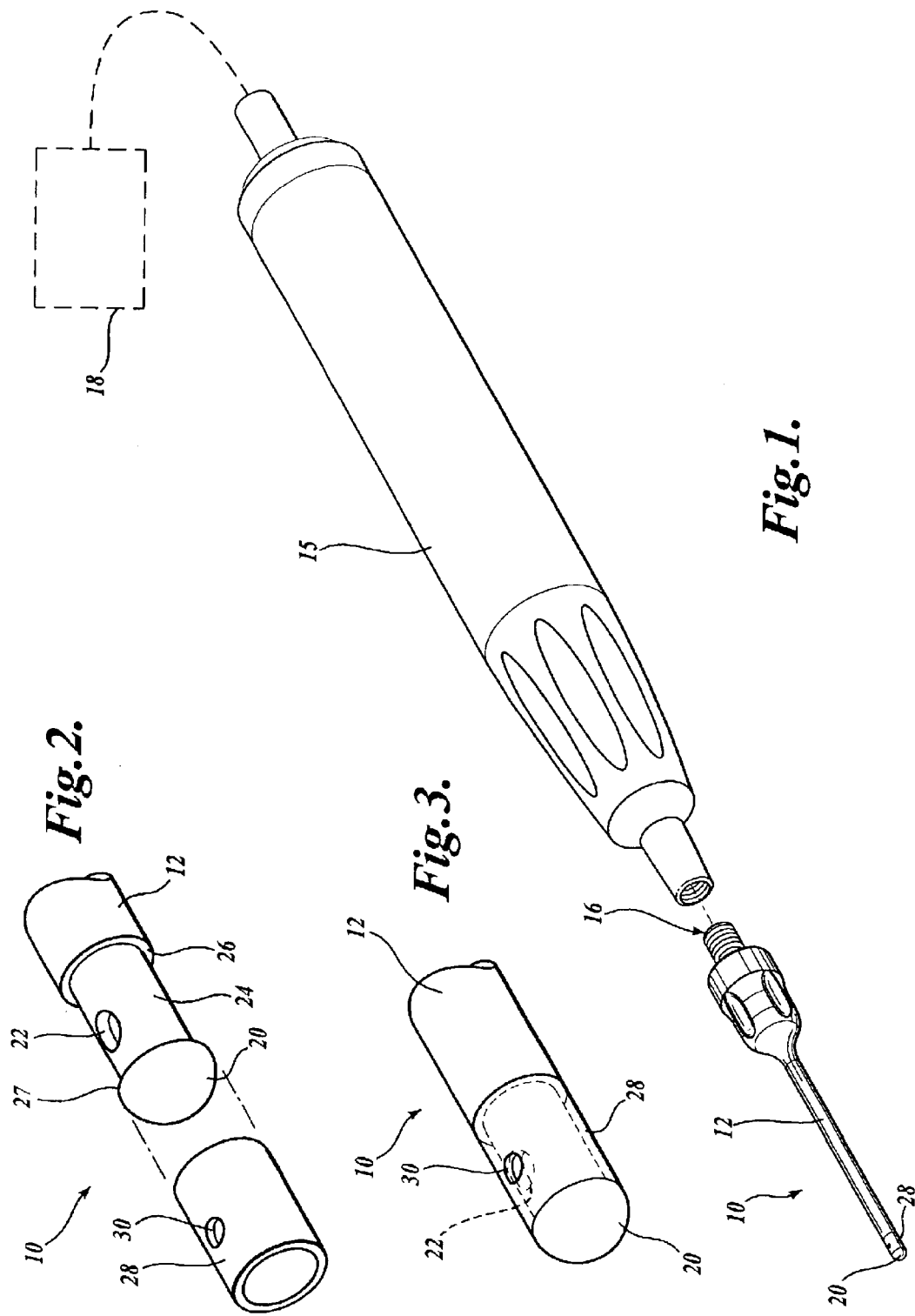

ASPIRATOR TIP

CROSS-REFERENCE TO RELATED APPLICATION

This application claims the benefit of U.S. Provisional Application No. 60/363,465, filed Mar. 11, 2002.

BACKGROUND OF THE INVENTION

Aspirators having small diameter distal tip portions are used during ophthalmic surgery, such as for removing cortical material, and cleaning and/or polishing the lens capsule, with or without simultaneous irrigation. During aspiration, the tip may engage fragile tissue of the lens capsule. The aspiration port of the tip can abrade or tear the capsule.

SUMMARY OF THE INVENTION

The present invention provides an improved aspirator tip having a rigid cannula wall with a side port for introduction of material into the bore of the cannula. A covering of resilient, flexible material is provided in the area of the side port, with a corresponding aperture aligned with the port of the cannula. In a preferred embodiment, the aperture of the resilient covering is somewhat smaller than the underlying cannula port, forming a resilient marginal portion that overhangs and surrounds the port. The resiliency of the covering around the port helps prevent abrading or tearing the lens capsule, permitting by deflection of the covering over the port, such as if the port is occluded.

BRIEF DESCRIPTION OF THE DRAWINGS

FIG. 1 is a somewhat diagrammatic top perspective of an aspirator handpiece and tip component in accordance with the present invention, with parts shown in exploded relationship.

FIG. 2 is an enlarged, fragmentary top perspective of the distal end portion of the aspirator tip component of FIG. 1, with parts shown in exploded relationship, and FIG. 3 is a corresponding enlarged, fragmentary top perspective with parts assembled.

DETAILED DESCRIPTION

The present invention provides an improved aspirator tip component of the type inserted into a lens capsule, such as for removing cortical material, and cleaning and/or polishing.

Figure 4:
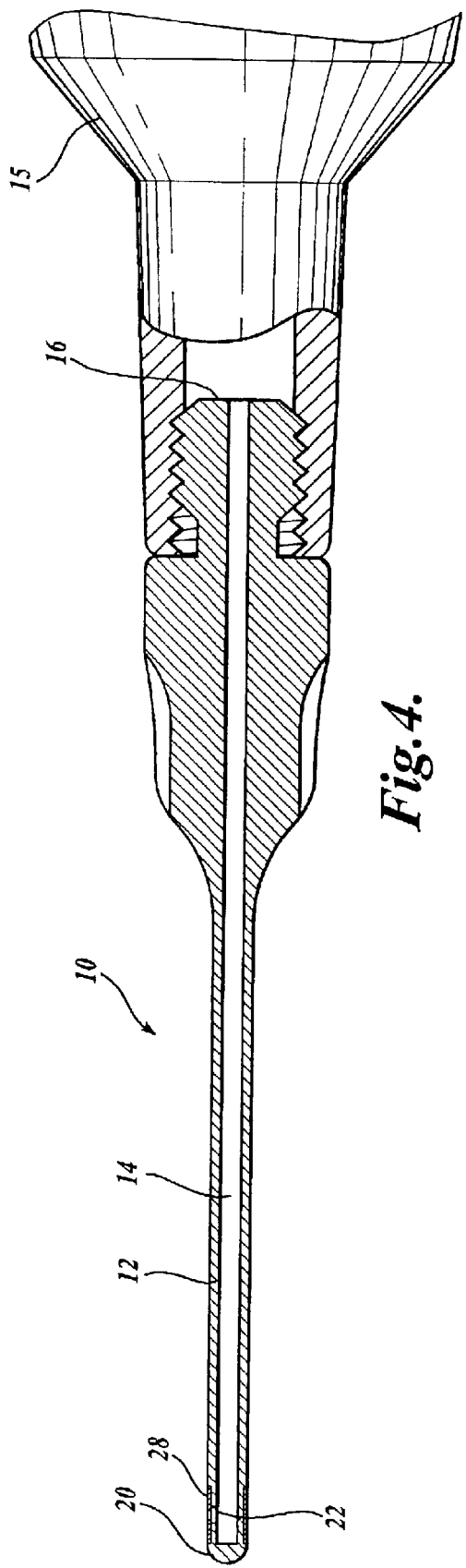
FIG. 4 is a fragmentary side elevation of the distal end portion of the handpiece and tip component of FIG. 1, with the parts assembled and with parts shown in section.
Figure 5:
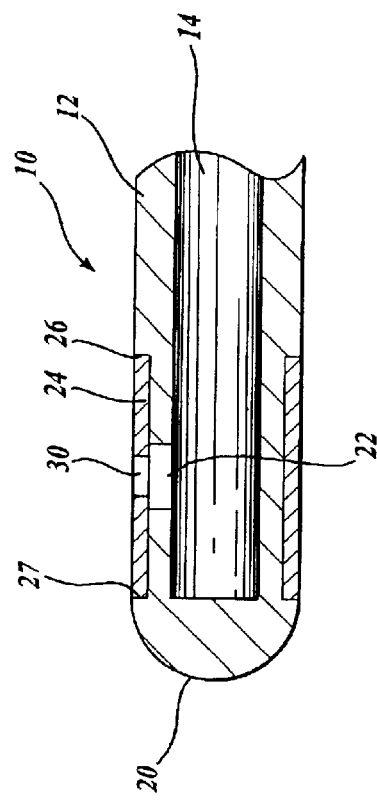
FIG. 5 is a further enlarged, fragmentary side elevation of the distal tip portion of the aspirator tip component, with parts shown in section.

With reference to FIGS. 1–5, an aspirator tip component 10 in accordance with the present invention includes a cannula 12 having a central bore 14 (FIGS. 4 and 5). The bore opens at the proximate end 16 of the tip component. The drawings are greatly enlarged in that the preferred embodiment of the aspirator tip component 10 will be sized for insertion through a narrow corneal slit during eye surgery. The proximate end 16 can connect to an aspiration handpiece 15 which, in turn, connects to a low pressure or vacuum source 18 indicated diagrammatically in FIG. 1.

Typically the cannula 12 is formed of a rigid material such as stainless steel. In the embodiment of FIGS. 1–5, the distal end 20 can be hemispherical or otherwise blunted so as not to cut or puncture delicate tissue. Distal end 20 closes the bore 14, and a side port 22 is provided communicating between the central bore 14 and the exterior of the cannula. The side port preferably is circular, but could be elongated in an alternative embodiment.

As best seen in FIG. 2, the diameter of the cannula 12 is reduced in the area of the side port 22, providing a circumferential groove 24 which extends both proximally and distally beyond port 22. Groove 24 terminates at an annular shoulder 26 at the proximate end and an annular shoulder 27 at the distal end. In this embodiment of the present invention, a covering in the form of a cylindrical sleeve 28 of resilient material such as silicone is fitted in the groove 24 of the cannula. The wall thickness of the cylindrical sleeve 28 preferably is essentially the same as the depth of the groove so that there is a smooth transition along the exterior of the cannula 12 and the exterior of the sleeve 28. The proximate and distal ends of the sleeve 28 butt against or are closely adjacent to the annular shoulders of the groove.

Sleeve 28 has an aperture 30 which is aligned with but preferably smaller than the port 22 of the cannula 12. This provides a marginal section that can deflect resiliently inward when aperture 30 is occluded. As compared to a rigid cannula, the soft covering is less likely to have burrs or rough edges which could tear delicate tissue, such as the posterior capsule. Similarly, if the instrument is brought into contact with delicate tissue, the deflection permitted around the port will lessen the possibility that a cut or tear will occur, even if there is limited movement of the tip after it contacts the tissue.

The sleeve 28 can be made translucent or clear so as to improve the visualization of material extraction, such as cortical material. The sleeve can be of sufficient resiliency as to be stretched over the end of the rigid cannula for installation, and can be secured in position by the resilient characteristics of the sleeve with or without adhesive or other manners of securing at the desired placement.

Figure 6:
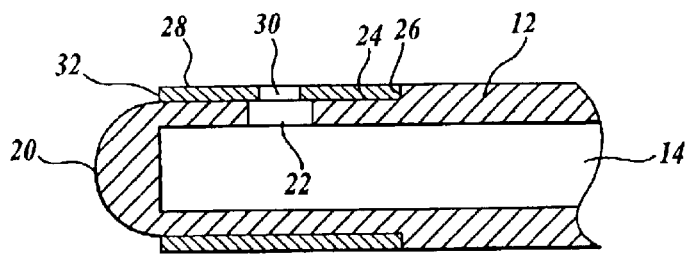
FIG. 6 is an enlarged, fragmentary sectional view corresponding to FIG. 5 but showing a second embodiment of the present invention.
Figure 7:
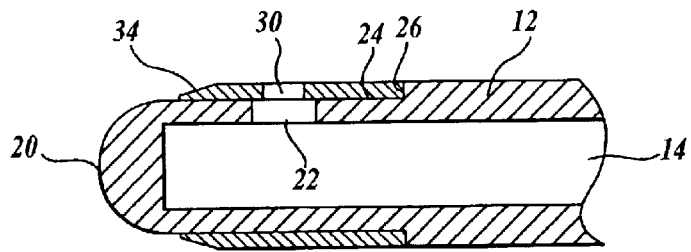
FIG. 7 is a corresponding fragmentary section showing a third embodiment.
Figure 8:
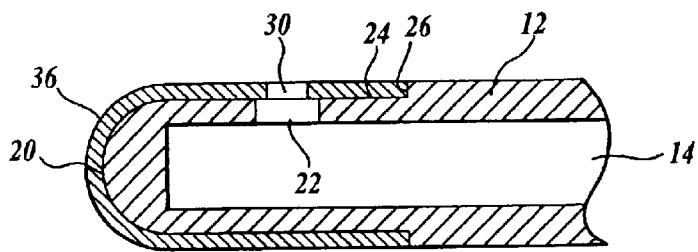
FIG. 8 is a corresponding fragmentary section showing a fourth embodiment.

In each of the embodiments of FIGS. 6–8, the reduced diameter portion 24 of the cannula is continued to the distal end 20 of the instrument, eliminating the distal annular shoulder but leaving the proximate annular shoulder 26. In the embodiment of FIG. 6, the sleeve 28 terminates at an abrupt, but soft, distal end 32. In the embodiment of FIG. 7, the distal end portion 34 tapers into the rounded or blunt cannula end 20. The sleeve also could extend almost precisely to the end 20, or slightly therebeyond. In the embodiment of FIG. 8, the sleeve is of constant thickness, but with a closed, generally hemispherical end 36 that covers the distal blunt end 20 of the cannula. In each instance, the sleeve has the aperture 30 of smaller diameter than the cannula port 22, such that a marginal portion of the resilient sleeve overhangs the inner port 22 and can be deflected.

Figure 9:
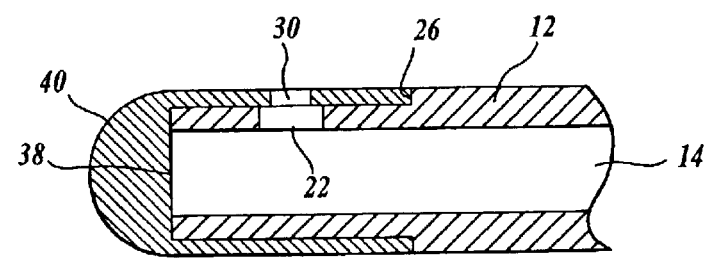
FIG. 9 is a corresponding fragmentary section showing a fifth embodiment.

In the embodiment of FIG. 9, the distal end 38 of the cannula 12 is open, with the sleeve being formed with a closed distal tip 40, preferably rounded or blunt. Such a closed tip could be stiffer than the material surrounding the side aperture 30.

Figure 10:
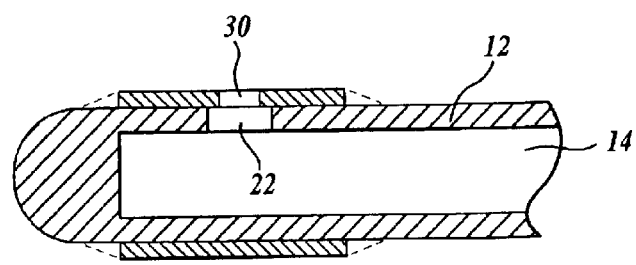
FIG. 10 is a corresponding fragmentary section showing a sixth embodiment.
Figure 11:
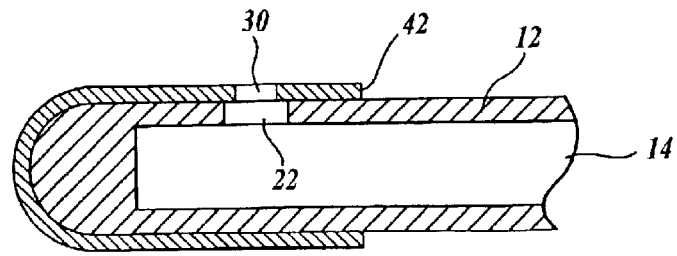
FIG. 11 is a corresponding fragmentary section showing a seventh embodiment.

With reference to FIGS. 10 and 11, another possibility is to provide the cannula 12 without a reduced diameter portion, but with the same larger diameter side port 22. A resilient, flexible cover in the form of a sleeve is fitted over the instrument and has the smaller aperture 30 aligned with the cannula side port 22. In that case, the distal end portion and/or proximate end portion of the sleeve cannula can be tapered toward the exterior of the cannula, as shown in broken lines in FIG. 10. If the cannula is provided with an open end, a sleeve having a closed end or an end cap (like FIG. 9) can be secured over the end of the cannula. In the embodiment of FIG. 11, the sleeve is identical to that shown in FIG. 8, the only difference being that the cannula 12 does not have a reduced diameter portion, such that the proximate end 42 of the sleeve is exposed.

Figure 12:
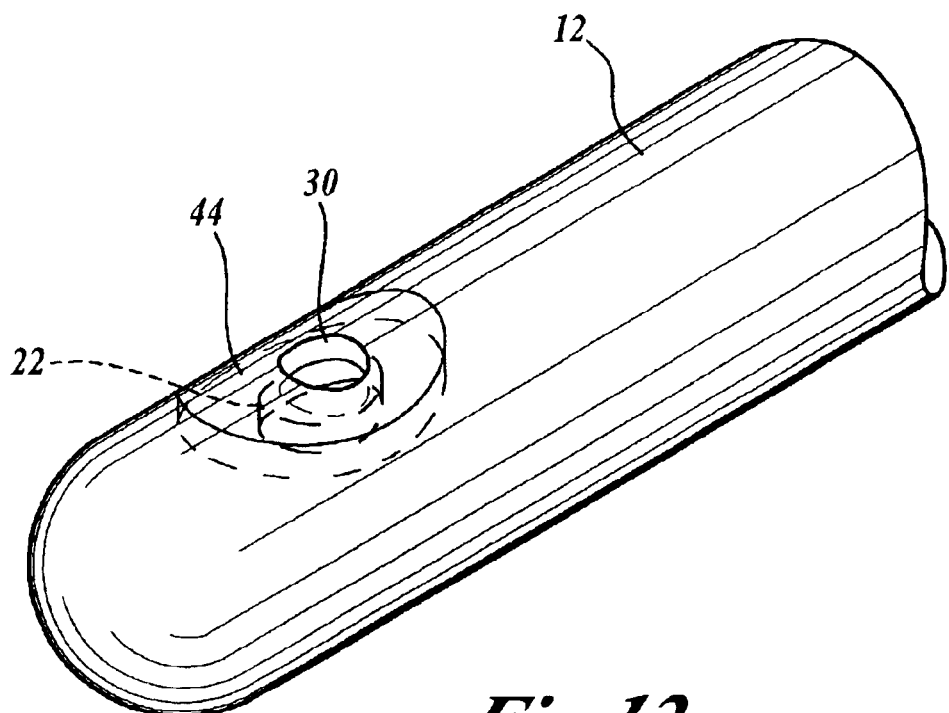
FIG. 12 is an enlarged top perspective of the distal tip portion of another embodiment of aspirator tip component in accordance with the present invention.

The previously described embodiments use coverings in the form of sleeves with cylindrical portions, at least part of which would fit over a generally cylindrical cannula. With reference to FIG. 12 another possibility is to use an inset piece 44 of resilient material in the area of the cannula or port 22, rather than a continuous sleeve. The cannula 12 can be provided with a recessed portion around the port 22, with the inset piece 44 closely received in the recess. The inset piece has the aperture 30 with a marginal portion overhanging the cannula port 22.

Figure 13:
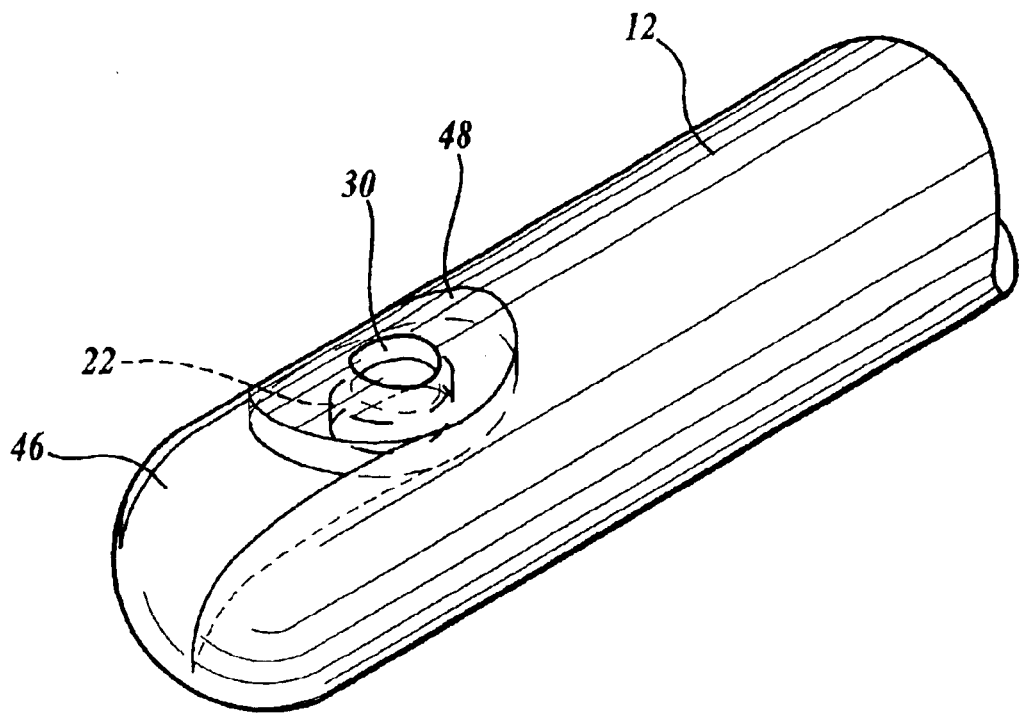
FIG. 13 is a corresponding enlarged fragmentary top perspective of a modified embodiment.

The embodiment of FIG. 13 is similar to the embodiment of FIG. 12, with the exception that the cannula 12 is formed with a longitudinally extending slot 46 in the area of a side port, with a handpiece inset piece 48 of resilient material fitted in the slot and having an aperture 30 of a smaller diameter than the cannula side port 22.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An aspirator tip comprising:
an elongated cannula having a peripheral wall forming a central bore, the cannula having an aspiration port opening transversely through the wall, the cannula being adapted to be connected to a low pressure source for aspiration of material through the port; and
a covering of flexible, resilient material extending over the port and having an aperture aligned with the port, the cannula port being larger than the aperture of the covering, such that the covering has a marginal portion adjacent to the aperture which marginal portion overhangs the port.

2. The tip defined in claim 1, in which the covering includes a cylindrical sleeve encircling the cannula in the area of the port.

3. The tip defined in claim 2, in which the cannula has an outer periphery of reduced diameter in the area of the port, the sleeve being fitted in the area of reduced diameter.

4. The tip defined in claim 3, in which the reduced diameter portion of the cannula continues to a distal end of the cannula.

5. The tip defined in claim 2, which the cannula has a peripheral groove in the area of the port forming longitudinally spaced, annular proximate and distal shoulders, the sleeve being closely fitted in the groove.

6. The tip defined in claim 5, in which the sleeve has a wall thickness approximately equal to the depth of the groove, so that there is a smooth transition along the exterior of the cannula and the exterior of the sleeve.

7. The tip defined in claim 5, in which the sleeve includes proximate and distal ends that are closely adjacent to the annular shoulders of the groove.

8. The tip defined in claim 1, in which the covering is translucent or clear for improved visualization of material entering the aspiration port.

9. The tip defined in claim 1, in which the cannula includes an integral closed distal end.

10. The tip defined in claim 1, in which the cannula includes an open distal end.

11. The tip defined in claim 10, in which the covering includes an end cap closing the distal end of the cannula.

12. The tip defined in claim 1, in which the covering includes a sleeve having proximate and distal ends, at least one of said ends being tapered toward the outer periphery of the cannula.

13. The tip defined in claim 1, in which the cannula has a recess in the area of the port, the covering including an inset piece of flexible, resilient material fitted in the recess.

14. The tip defined in claim 13, which the recess extends longitudinally of the cannula from the port toward the distal end of the cannula.

15. An aspirator tip comprising:
an elongated cannula having a peripheral wall forming a central bore, the cannula having an aspiration port opening transversely through the wall; and
a covering of flexible, resilient material extending over the port and having an aperture aligned with the port, the covering including a cylindrical sleeve encircling the cannula in the area of the port, the cannula having an outer periphery of reduced diameter in the area of the port, the sleeve being fitted in the area of reduced diameter, the reduced diameter portion of the cannula continuing to a distal end of the cannula, the cannula having a peripheral groove in the area of the port forming longitudinally spaced, annular proximate and distal shoulders, the sleeve being closely fitted in the groove, the sleeve having a wall thickness approximately equal to the depth of the groove, so that there is a smooth transition along the exterior of the cannula and the exterior of the sleeve.

* * * * *